United States Patent [19]

Berke et al.

[11] Patent Number: 5,084,245

[45] Date of Patent: Jan. 28, 1992

[54] ASSAY DEVICE FOR SWAB BORNE ANALYTES

[75] Inventors: Carl M. Berke, Boston; Donald J. Lennon, Hopedale; Paul B. Foster, Quincy; Gary W. Boys, Northboro, all of Mass.

[73] Assignee: Hygeia Sciences, Inc., Newton, Mass.

[21] Appl. No.: 630,432

[22] Filed: Dec. 20, 1990

Related U.S. Application Data

[63] Continuation of Ser. No. 267,890, Nov. 7, 1988, abandoned.

[51] Int. Cl.$^5$ ............................................. G01N 15/00
[52] U.S. Cl. .................................... 422/61; 422/101; 436/808; 436/810; 435/810; 435/295
[58] Field of Search ..................... 422/61, 101, 102; 435/810, 295, 211; 436/808, 810

[56] References Cited

U.S. PATENT DOCUMENTS

| | | |
|---|---|---|
| 4,657,869 | 4/1987 | Richards et al. ............... 436/810 |
| 4,847,199 | 7/1989 | Snyder et al. .................. 422/61 |
| 4,912,034 | 3/1990 | Kalra et al. .................... 422/61 |
| 4,912,048 | 3/1990 | Smith et al. ................... 435/296 |

Primary Examiner—David L. Lacey
Assistant Examiner—Abanti B. Singla
Attorney, Agent, or Firm—Staas & Halsey

[57] ABSTRACT

A disposable, pre-packaged device as particularly suitable for conducting diagnostic procedures based on immunological reactions using specimens gathered up in the absorbent tip of a swab. The device is made up of a base component upon which a sample sensitive element is mounted and a guide member that is normally mounted on the base component in covering relationship to the reactive element. The guide member includes structure which defines an elongated passageway extending therethrough. One end of the passageway is positioned in close proximity to the sensitive element when the member is mounted on the base component. The other end of the passageway opens outwardly of the guide member. In using the device, the swab tip is pushed through the passageway and toward the sensitive element using the stick of the swab. A number of ribs are positioned in the passageway adjacent the sensitive element to squeeze the tip and express fluid therefrom as the tip is pushed toward the sensitive element. Thus, the liquid in the swab tip is expressed therefrom and brought into intimate contact with the sensitive element. The results of the test are visually observable by removing the guide member from the base component to uncover the sensitive element.

34 Claims, 4 Drawing Sheets

ASSAY DEVICE FOR SWAB BORNE ANALYTES

Related Applications

This application is a continuation of application Ser. No. 07/267,890, filed Nov. 7, 1988, and now abandoned.

BACKGROUND OF THE INVENTION

1. Field of the Invention

The present invention relates to devices for conducting assay procedures. More particularly, the invention relates to disposable, pre-packaged devices which are particularly suitable for conducting diagnostic procedures based on immunological reactions using specimens gathered on swabs at remote sites such as physician's offices and homes of users.

2. Description of the Prior Art

Since the important discovery of Milstein and Kohler reported in *Nature* 256: 495–497, 1975, the development of highly sensitive and specific immunoassay procedures has proceeded at a rapid pace. In fields such as clinical medicine, forensic sciences, environmental quality testing, food quality assurance, drug testing and other related areas, it has become possible to determine the presence and/or amount of trace substances in test samples even when such substances are present in very low concentrations in the order of parts per million, or even less. The development of non-radioactive labels or markers, such as enzyme color formers, has facilitated the use of immunoassay diagnostic procedures outside of laboratory settings and in remote sites such as physician's offices and even the homes of the users. In the physician's office, immunological procedures are useful for providing rapid, simple assays which may be performed while the patient is still in the office so that the diagnosis can be accomplished without delay and treatment instituted during a single visit. Without such simple assays, it has often been necessary for the physician to collect a sample from a patient during a first visit and to have the sample analyzed by a clinical laboratory with the results reported back to the physician by the laboratory at a later time. In the meanwhile, the patient was sent home and was required to return for a second visit with the physician in order to receive appropriate treatment and/or medication. Manifestly, such delay was inefficient and inappropriate and in some cases even life threatening.

Home testing has become desirable to facilitate testing by the consumer in the privacy of his or her own home. The results of such testing might, for example, indicate the necessity or lack of necessity of a visit to the physician. Examples of useful tests for the "at home" market include tests for pregnancy, ovulation, streptococcus infection and other infections which are detectable by analysis of body fluids such as urine, saliva, throat fluids, pus, vaginal fluids, blood or other appropriate test samples.

For remote site testing, assuming appropriate sensitivity and specificity can be achieved, there are at least three other requirements for practical assay procedures. The first of these desirable factors is speed in that the assay must be performed in an acceptably short period of time, the shorter the better. Stability is also a desirable feature in that the components of the assay should be stable for an extended period of time without refrigeration or special handling. Finally, from a commercial view point it is desirable that the test be convenient to use and as simple as possible requiring only minimal or no instrumentation and precluding mistakes and poor performance resulting in incorrect interpretations.

One of the difficulties encountered in the development of test devices for remote site testing is the provision of a practical pre-packaged disposable device to facilitate efficient, relatively inexpensive, fool proof test procedures. This, of course, requires a device which is inexpensive to construct, which has a shelf life appropriate to the commercial use thereof, which is protected against contamination during handling, which may be simply and conveniently utilized when the appropriate time arises, and which may conveniently and safely be used by even untrained persons.

The device illustrated in U.S. Pat. No. 4,632,901 addresses some of these problems and is available commercially; however, the device has a number of deficiencies including the fact that it is useful only in connection with urine or other pourable fluid samples. Another device for testing pourable fluid samples is illustrated in the co-pending, commonly owned application of Lennon and Murphy, Ser. No. 107,240, filed Oct. 29, 1987.

Other prior single test devices are illustrated in U.S. Pat. Nos. 4,366,241 and 4,623,461. However, these devices are of limited application and have excessive complexity.

None of these prior art devices addresses the particularly difficult set of problems that are encountered when a sample is collected on a swab or the like for delivery to the test device, such as is necessary in the case of a strep throat test, for example. Rather, to use prior devices with a test sample collected on a swab, it was generally necessary to utilize techniques involving manual expression of the specimen fluid from the swab to form a pourable liquid test mixture or the streaking of the fluid from the swab onto an agar plate.

SUMMARY OF THE INVENTION

The present invention provides relief from many of the shortcomings of the prior devices described above. In this regard the invention provides a simplified, pre-packaged, disposable test device wherein an analyte in a swab tip may be brought directly into intimate contact with an element that is sensitive to the analyte, such as a porous capture media element, where products of the procedure are created or captured and may be displayed for direct visual observation.

In accordance with the invention, a disposable, pre-packaged device is provided for conducting an assay or analytical procedure or test in conjunction with a swab comprising an elongated stick and an adsorbent tip used to collect a sample containing an analyte. In the performance of the assay or analytical procedure for which the device of the invention is designed, a fluid material containing a test analyte or a derivative thereof is carried in the swab tip and is brought into intimate contact with an element that is sensitive to the analyte.

The device of the invention comprises a base component on which a sensitive element is mounted and a guide member normally mounted on the base component in covering relationship to the sensitive element. The guide member is removable from the base component to permit inspection of the sensitive element upon completion of the test. The guide member includes structure defining an elongated passageway extending therethrough and such passageway has one end positioned in close proximity to the sensitive element when the member is mounted on the base component. A second end of the guide member opens outwardly of the guide member.

The structure which defines the elongated passageway includes means adjacent the second end of the passageway for receiving the tip of a swab containing a sample or derivative thereof as the tip of the swab is manually pushed axially of the swab into the passageway and along the latter toward said one end thereof. Means are provided in the passageway adjacent to, but preferably slightly spaced from said one end of the latter, for squeezing the tip to express fluid therefrom as the tip is pushed toward the element using the stick of the swab. The passageway is preferably generally circular in cross-sectional configuration and the means for squeezing the tip preferably comprises rib means which project radially inwardly of the passageway to restrict the cross-sectional area of the latter.

The rib means may comprise a plurality of circumferentially spaced ribs which extend along the passageway and the same may be uniformly distributed around the circumference of the passageway. Each rib may have a length which is approximately ½ to 1½ times the overall length of the swab tip; however, the relationship between the length of the ribs and the length of the swab tip is not critical so long as the ribs operate to express the fluid from the swab tip. The ribs may be arranged so as to present channels therebetween extending along the passageway to facilitate flow of expressed fluid toward the sensitive element.

In accordance with a preferred aspect of the invention, the receiving means in the passageway may comprise means defining a generally conically shaped tip receiving chamber having an outer opening which is larger in diameter than the swab tip and a smaller inner opening. Moreover, the device may include a prefilter carried by the guide member in covering relationship to said one end of the passageway. The base component and the guide member preferably include means which normally holds the base component and the guide members together to conduct a test and permits separation of the component and the member at the completion of the test. The holding means may comprise a well in the base component and a complimentarily shaped projection o the guide member. The projection is normally received in the well and held in place there by frictional engagement and/or a snap-fit mechanical engagement.

In a specific preferred aspect of one embodiment of the invention, the well may have a circular sidewall and a floor, and the projection may have a cylindrical peripheral surface and a distal end. In this aspect of the invention, the sensitive element may be mounted on the floor of the well and said one end of the passageway may be located at the distal end of the projection, the frictional engagement for holding the member and the component together being between the sidewall of the well and the external surface of the projection. Vent means comprising a small groove extending from the floor of the well and upwardly along the sidewall of the latter may be provided for venting air from the well during the conduct of the test.

The device of the invention is particularly useful in connection with immunoassay procedures wherein an adsorbent tip is used to collect a sample and wherein a fluid material containing an immunoreactive constituent that is borne by the tip is brought into intimate contact with a sensitive porous capture element. In this preferred aspect of the invention, the device may comprise a base component which has an upper surface and includes an internal sidewall and a floor defining a test well that opens upwardly of the upper surface. A porous capture element is disposed on the floor at the bottom of the well.

The device further comprises a guide member which includes a projection having an outer surface with a shape which corresponds with the shape of the internal sidewall of the well. The projection is initially and normally positioned within the well with its outer surface engaging the internal sidewall of the well. The projection is removable from the well for visual inspection of the capture element at the conclusion of the test.

The guide member also preferably includes structure defining an elongated passageway extending therethrough. One end of the passageway is disposed in close proximity to the capture element on the floor of the well when the projection is positioned in the well. The other end of the passageway opens upwardly of the device. The structure which defines an elongated passageway comprises means adjacent said other end of the passageway for receiving the tip of the swab as the same is manually pushed axially of the swab and into the passageway using the swab stick. The structure defining the elongated passageway also comprises means for directing the swab tip toward the sensitive capture element as the swab tip is pushed along the passageway by the stick, and means for squeezing the tip to express fluid therefrom as the tip is pushed toward the capture element.

In a particularly preferred form of the invention, the device of the invention may comprise a base component and a guide member which are each molded from a thermoplastic material.

DETAILED DESCRIPTION OF THE INVENTION

Figure 1:
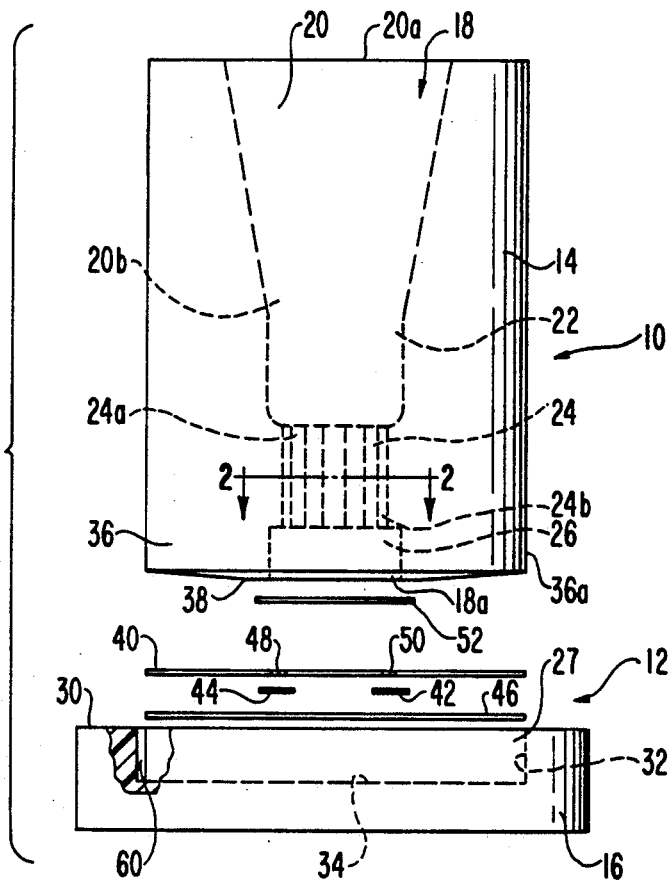
FIG. 1 is an exploded, elevational view illustrating a disposable, pre-packaged device which embodies the principles and concepts of the present invention and showing the constructural details of and the operational relationships between the guide member, the base component and the sensitive element.

The concepts and principles of the present invention are embodied in a disposable, pre-packaged device 10 which is illustrated in FIG. 1 through 5 of the drawings. Device 10 is useful for conducting an assay or analytical test in conjunction with a swab used for collection of a sample containing an analyte. In the performance of the test, a fluid material containing the analyte or a derivative thereof is carried in the swab tip and is brought into intimate contact with a sensitive element 12. Device 10 is particularly useful for conducting an immunoassay procedure; however, the exact type of procedure or protocol utilized is not important for purposes of the present invention since device 10 may be used to facilitate any sort of procedure which results in the production of a specific signal when an analyte or a derivative of an analyte is brought into contact with a contact element that is specifically sensitive to the presence of the analyte or derivative.

In the sense of the present invention, the term sensitive simply means that the presence of the analyte or derivative causes a detectable signal to be present on the element. For example, the analyte and/or its derivative may cause production of a collectible or filterable phase that incorporates a tag of some sort to indicate a positive or negative test result and such phase is then captured by the sensitive element. The sensitivity may be the result of a reactive ingredient initially present on the element or may be the result of the element simply being able to physically capture a product formed by the test.

Generally speaking, the device 10 of the present invention may be utilized in connection with procedures which employ a visually detectable colored or color forming tag such as an enzyme or metal sol particle tag to indicate the occurrence or non-occurrence of a specific immunoreaction. It is also within the perceived usefulness of the invention that the device might well be employed in connection with procedures wherein a reactant is tagged with an instrument detectable tag such as a radioactive isotope, a fluorescent material or a chemiluminescent material. Additionally, the device should be useful in connection with purely chemical tests wherein an analyte simply causes a chemical change in the sensitive element or a material thereon.

Immunoassay kits employing enzyme markers are presently commercially available for determining such conditions as pregnancy and ovulation in the physician's office and in the home of the user. Such kits are described in said '901 patent and in said co-pending application Ser. No. 107,240 abandoned Sept. 8, 1989. In the '901 patent and in some of the procedures of the '240 application, an enzyme labelled antibody reacts with an antigen to form an immunocomposite that is collected on a porous membrane upon further reaction of the antigen with another antibody immobilized on the porous capture membrane. The enzyme tag enters into a reaction system with chemicals fixed on the membrane to produce a visible color.

In the co-pending application of Cole, Davis and Sigillo, entitled "Metal Sol Capture Immunoassay Procedure, Kit For Use Therein and Captured Metal Containing Composite", Ser. No. 105,285, filed Oct. 7, 1987, now U.S. Pat. No. 4,859,612, which application is also assigned to the assignee of the present application, a metal particle is utilized as the label and a collectible, solid phase, metal containing composite is formed. The composite may be collected by filtration on a filter element or the like where the presence of analyte in the original sample is determined or detected by evaluating, through direct visual examination, the presence of metal in the collected solid phase. In the sense of the present invention, the filter element is sensitive to the presence of the immunocomposite because its pores are so small that the immunocomposite cannot pass therethrough.

Another disposable, pre-packaged device for conducting immunoassay procedures wherein the analyte is collected on a swab is described in the co-pending application of Lennon and Foster, entitled "Swab Expressor Immunoassay Device," Ser. No. 191,158, filed May 6, 1988, which application is also assigned to the assignee of the present application.

The entireties of the disclosures of said co-pending applications Ser. Nos. 105,285, 107,240 and 191,158 now U.S. Pat. No. 4,963,325 are hereby specifically incorporated herein by reference.

In a preferred form of the invention, the device 10 may comprise a cylindrical guide member in the form of a barrel 14 and a base component 16. Barrel 14 includes internal structure defining an elongated passageway 18 extending through the member. Passageway 18 includes a generally frustoconically shaped chamber 20 at the upper end of the barrel, a central section 22 which is circular in cross-sectional configuration, a ribbed section 24 having a function which will be explained in detail hereinbelow and a section 26 which is circular in cross-sectional configuration.

Figure 2:
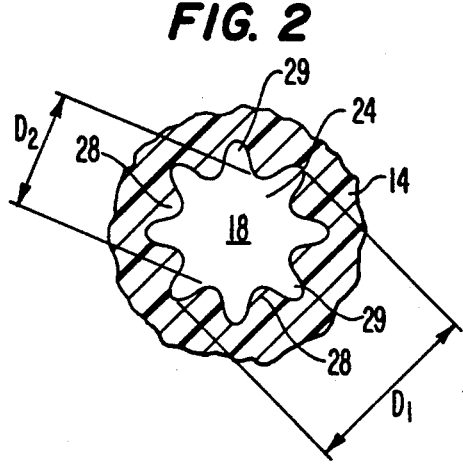
FIG. 2 is a cross-sectional view taken along the line 2—2 of FIG. 1.

With reference to FIG. 2, it can be seen that the cross-sectional configuration of section 24 presents a plurality of circumferentially spaced ribs 28. The cross-sectional configuration of section 24 is constant and thus the ribs 28 extend along the passageway from the upper end 24a of section 24 to the lower end 24b thereof. Also, as can be seen viewing FIG. 2, the ribs 28 are uniformly distributed around the circumference of the passageway and the same are configured to present channels 29 therebetween. Channels 29, like ribs 28, extend along passageway 18 from upper end 24a of section 24 to the lower end 24b thereof. Ribs 28 thus present means projecting radially inwardly of passageway 18 to restrict the crosssectional area thereof.

Figure 4:
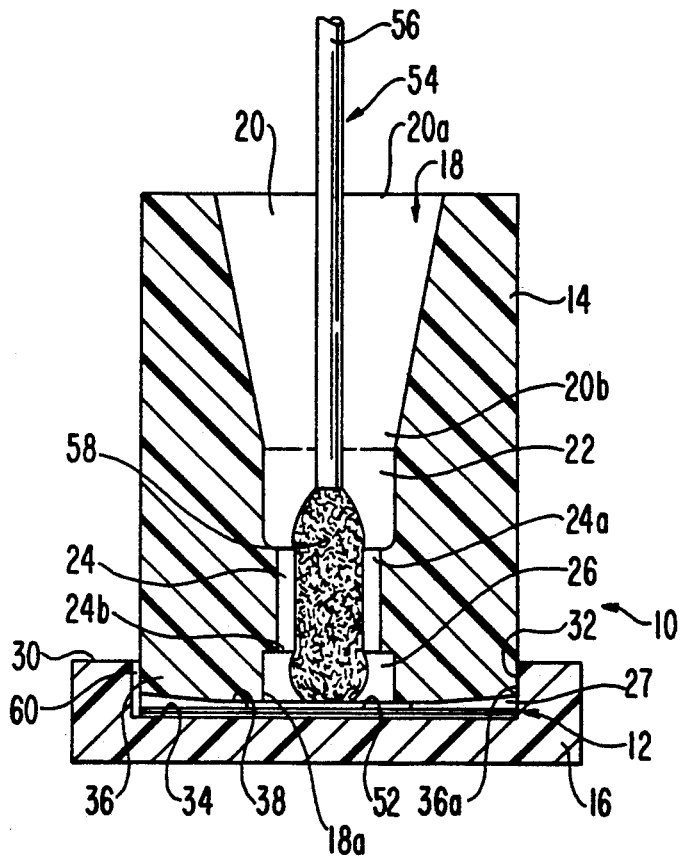
FIG. 4 is a cross-sectional view taken along the line 4—4 of FIG. 3 and illustrating the internal details of the device and the operational relationships between the components of the device and the swab.

As can be seen viewing FIG. 4, chamber 20 has an upper or outer opening 20a that is larger in cross-sectional dimension than the opening 20b at the lower end of chamber 20.

Figure 3:
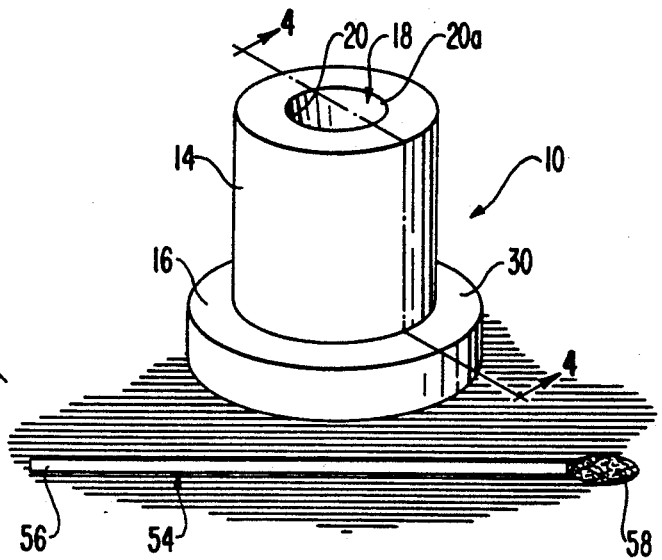
FIG. 3 is an isometric view of the device of the invention and a swab which is used in conjunction with the device of the invention.

Barrel 14 is normally mounted on base 16 during performance of a test procedure. This cooperative relationship is illustrated in FIGS. 3 and 4. To facilitate such mounting the base 16 is provided with a circular test well 27 which opens upwardly of the upper surface 30 of the base 16. Well 27 is defined by a generally circular internal sidewall 32 and a floor 34. Floor 34 cannot be seen in FIG. 5 because it is covered by sensitive element 12 which is thus mounted on or carried by floor 34 in well 27 of base 16.

As can be seen viewing FIGS. 1 and 4, the lower end of barrel 14 is in the form of a projection 36 which projects into well 27 when barrel 14 is mounted in operating disposition on base 16. Projection 36 has an outer cylindrical external surface 36a which frictionally engages wall 32 when projection 36 is received within well 27. Barrel 14 has a distal end 38 which is disposed in immediate proximity relative to element 12 when barrel 14 is mounted on base 16 in operating disposition.

A prefilter 52 is mounted at distal end 38 of barrel 14 in covering relationship to the lower end 18a of passageway 18.

Device 10 is utilized for conducting an immunoassay test in conjunction with a swab 54 which comprises an elongated stick 56 and an absorbent or porous tip 58. In performing a test procedure, swab tip 58 is pushed downwardly manually through passageway 18 and toward the element 12. Thus, swab 54 assumes the position illustrated in FIG. 4 during the conduct of the test.

A semi-circular groove 60 is provided in sidewall 32. Groove 60 extends upwardly in well 27 from floor 34 and along sidewall 32 to surface 30, as can particularly be seen in FIGS. 1 and 4. Groove 60 cooperates with the immediately adjacent portions of surface 36a to provide a defined vent for venting air from well 27 during the conduct of a test procedure.

As indicated above, barrel 14 is normally mounted on base 16 in covering relationship to element 12 during the conduct of a test procedure. External surface 36a of projection 36 of barrel 14 is complimentarily and correspondingly shaped relative to sidewall 32 so that surface 36a and internal sidewall 32 of base 16 provide a mated, frictional engagement to releasably hold barrel 14 and base 16 together. Barrel 14 and base 16 are therefore normally held together by friction with distal end 38 of barrel 14 disposed in covering relationship relative to element 12 during the conduct of a test procedure. On the other hand, the frictional fit between projection 36 and well 27 is such that barrel 14 may readily be separated from base 16 at the conclusion of the test procedure to permit element 12 to be inspected visually.

Barrel 14 and base 16 may preferably be constructed of plastic or glass or any other suitably inert material, and these components may be made by injection molding of a thermoplastic material such as styrene, delrin or polyester. The only real limitation on the materials of construction for device 10 is that the same must be sturdy and stable and inert to the test reactants and reaction products.

In the preferred form of the invention, as discussed above device 10 may be utilized for conduct of an immunoassay procedure. Thus, element 12 may preferably comprise a capture media element assemblage that is best illustrated in exploded view in FIG. 1 where it can be seen that element or assemblage 12 comprises a flow director 40 having ports or holes 48 and 50 therein, capture elements 42 and 44 disposed in alignment with holes 48 and 50, and an absorbent pad 46. On the other hand, element 12 may take any number of other physical forms so long as the same comprises a component that is sensitive to the presence of analyte or derivative to be detected or determined pursuant to the test.

Absorbent pad 46 may be constructed of an absorbent material having capillary passages extending therethrough in a diversity of directions which are both transverse to and generally parallel to the surfaces of pad 46. There are a number of materials which are well known to those of skill in the art to which the present invention pertains that may be used to construct absorbent pad 46. Such materials include hydrophilic polymers, particulate adsorbents, glass fibers, cotton fibers, cellulose fibers, wood pulp and/or sponge. Other materials which may find use as pad 46 include polysaccharides, for example cellulosic materials, such as paper and cellulose acetate. Cellulose acetate fibers arranged in the same manner as in a cigarette filter may be utilized to construct absorbent pad 46. Another useful material is the absorbent material used in a tampon. A particularly useful material for construction of pad 46 is a cellulosic pad material, approximately 0.036" thick, available commercially from Schleicher and Schuell. In any event, the important features of the materials useful in the construction of pad 46 are simply that the same be capable of absorbing a substantial quantity of fluid materials and that the same possess sufficient structural integrity to facilitate the initial construction of assemblage 12. Further useful absorbent materials are disclosed, for example, in U.S. Pat. Nos. 4,246,339; 4,623,461; 4,632,901 and 4,366,241.

The porous capture media elements 42 and 44 may also take any one of several different forms, depending on the type of procedure which is utilized. For example, if the procedure is an immunoassay that involves an immobilized antibody ELISA technique, elements 42 and 44 may be membranes having a co-reactant antibody for the analyte to be assayed in the test liquid sample immobilized on the internal and external surfaces thereof. Thus the membrane is sensitive to the presence of the analyte. Such membranes are utilized in the procedures disclosed in U.S. Pat. No. 4,246,339 and in International PCT Publication No. WO85/05451 (International Application No. PCT/US85/00870). Membranes useful in connection with such procedures are fully disclosed and described in U.S. Pat. No. 4,340,479. Manifestly, methods for binding immunoreactants to such membranes are well known to those skilled in the art. Elements 42 and 44 may preferably be about 0.006" thick and the same may be constructed from activated microporous nylon membrane material available commercially under the tradename "Gelman Ultrabind."

In another form of the invention, porous capture media elements 42 and 44 may be composed of such things as glass fiber filters (Whatman GF/A), regenerated cellulosic membranes (Schleicher and Schuell) and microporous membranes (Millipore MF series membranes HAWP, SSWP, SMWP and SCWP with pore sizes of 0.45, 3, 5 and 8 microns respectively). All of these materials have been successfully utilized for capturing and collecting a solid phase product resulting from an immunoassay procedure. In particular such materials have been found to be useful for capturing the collectible, solid phase, metal containing composites which result from the immunoassay procedures described in said co-pending and co-assigned '285 application of Cole et al. Manifestly, in such process, the porous capture media element is sensitive to the presence of the composites simply because it comprises a filter element having pores of a size to prevent passage of the reaction products to be captured and collected. Accordingly, the desired reaction products accumulate on the surface of the sensitive element and are available there for visual inspection.

Flow director 40 may be constructed of a non-adsorptive, transparent polyester film such as Mylar Flow director 40 may be approximately 2-4 mil in thickness. The flow directing holes 48 and 50 should be positioned so as to directly overly the corresponding elements 44 and 42 and the latter should simply be large enough so that the liquid flowing through holes 48 and 50 is directed appropriately into and through the pores of the elements 42 and 44.

Figure 5:
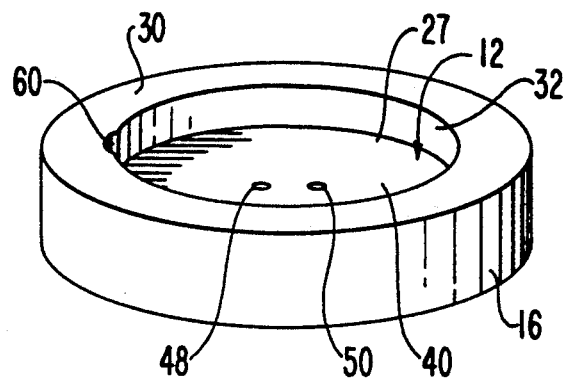
FIG. 5 is an enlarged isometric view of the base component with the guide member removed therefrom to permit inspection of the sensitive element.

The capture media element assemblage 12 is illustrated in an exploded condition in FIG. 1, and to facilitate assembly thereof, the beneath side of flow director 40 may be coated with an acrylic adhesive, for example, so as to hold the elements 42 and 44 in place and to hold the flow director 40 tightly against the absorbent pad 46 so that the assemblage 12 may be readily manipulated and handled as a single component. Manifestly, an adhesive material may be applied to the back of absorbent layer 46 so as to adhere assemblage 12 to floor 34 of base 16 in the desired location as illustrated in FIGS. 4 and 5.

Prefilter 52 may preferably be a microporous nylon membrane having a porosity in the order of approximately 0.5 to 5.0 microns. Such membranes are commercially available. A preferred membrane for use in the construction of filter 52 is available under the trade name "Pall LoProdyne". In the preferred form of the invention, the nylon membrane utilized to form the filter 52 may be approximately 0.006" thick and the same may be held in place on the distal end 38 of barrel 14, as illustrated in FIG. 4, using an adhesive. Alternatively, filter 52 may be attached to distal end 38 of barrel 14 by ultra-sonic welding. In any case, filter 52 is disposed in covering relationship to end 20a of passageway 20 and serves to remove debris present in the test fluid and which might interfere with the sensitivity and specificity of the capture element and/or the operation of the test materials and procedures. Filter 52 is preferably attached onto the distal end 38 of barrel 14 to facilitate movement to an out-of-the-way-position when the device is opened by removal of barrel 14 from base 16 so that the test results showing on element 12 may be read. When barrel 14 and base 16 are assembled in test conducting relationship with projection 36 extending into well 27, distal end 38 presses prefilter 52 tightly against flow director 40 such that filter 52 and the components of element 12 are in close capillary contact.

In the operation of device 10, a specimen is collected on absorbent tip 58 of swab 54. For example, in conducting a test for strep throat, a swab is utilized to swab the tonsil area. The swab may then be contacted with appropriate immunoreagents in a liquid system and the mixture may then be allowed to incubate for a period of time, all as is well known to those skilled in the immunoassay art. After a sufficient incubation period, during which the swab tip may remain in contact with the liquid system containing other immunoreagents, the reaction mixture, or at least a portion thereof, will have been gathered up in and absorbed by absorbent tip 58.

In the form of the invention wherein an antibody is immobilized on one or the other or both of elements 42 and 44, the reaction fluid in the swab tip may simply contain unreacted test analyte to be determined or a reactive derivative immunocomposite comprising a labelled antibody bound to the test analyte. On the other hand, in the form of the invention which might utilize the gold sol capture immunoassay procedure described in said '285 application of Cole et al., the reaction fluid in the swab tip may contain an immunocomposite comprising a completed derivative sandwich reaction product consisting of a labelled antibody, the test analyte, and a second antibody bound to a solid particle too large to traverse the pores of the capture elements 42 and 44.

The swab which has adsorbed the liquid reaction mixture is then inserted into device 10 so as to assume the position illustrated in FIG. 4. To facilitate such insertion, chamber 20 presents means at the upper end of passageway 18 for receiving the tip of a swab containing fluid as a tip, such as tip 58, is pushed manually in a direction axially of swab 54 and into and along passageway 18. In this regard, chamber 20 is a generally conically shaped tip receiving chamber and the opening 20a thereof provides an outer opening which is larger in cross-sectional dimension than tip 58 of swab 54. Manifestly, as swab 54 is manually pushed downwardly through passageway 18 utilizing stick 56 which extends outside of barrel 14, the tip 58 is directed toward element 12. Ribs 28 in section 24 of passageway 18 provide means adjacent end 18a of passageway 18 for squeezing swab tip 58 to express fluid therefrom as tip 58 is pushed downwardly toward element 12. Channels 29 prevent the liquid in swab tip 58 from welling up and thus facilitate the flow of expressed fluid downwardly through prefilter 52 and toward element 12. As illustrated in FIG. 4, the length of each rib 28 is preferably approximately ½ the length of the swab tip. Moreover, with reference to FIG. 2, the major cross-sectional dimension $D_1$ of section 24 of passageway 18 at the bottoms of channels 29 may preferably be approximately 0.208 inch and the minor dimension $D_2$ measured at the apex of each rib 28 may be approximately 0.166 inch to thus accommodate a conventional swab 54 having an absorbent tip 58 with a diameter of approximately 0.18 inch. In this same connection, barrel 14 may be 1 inch in length and the same may have an outside diameter of 0.75 inch. Additionally, sections 22 and 26 of passageway 18 may be circular passageways, each having a diameter of approximately 0.25 inch. In this regard, it should be noted that the swab 54 may have a length of approximately 6 inches so that approximately a 5 inch length of stick 56 is disposed externally of device 10 when swab tip 58 has been received through passageway 22 and is in intimate positional relationship relative to element 12, as illustrated in FIG. 4. Notch 60 may be semicircular and have a diameter of approximately 0.05 inch in order to facilitate venting of well 28 during the test procedure.

As tip 58 of swab 54 is pushed into intimate contact with filter 52 which covers end 18a of passageway 18, absorbent tip 58 is essentially in direct capillary communication with elements 42 and 44 of capture media element assemblage 12. Thus, liquid is expressed from tip 58 by the pressure exerted by ribs 28 and the downward manual pressure on stick 56 pushing tip 58 against filter 52. The expressed liquid is channeled by channels 29 of passageway 18 and by passageway section 26 so that the same flows through filter 52 and then through elements 42 and 44. The movement of the liquid through elements 42 and 44 is enhanced by the action of pad 46 which, because of its absorbent structure and nature, imbibes the liquid and pulls it through elements 42 and 44.

As is known to those of skill in the art to which the present invention pertains, elements 42 and 44 may consist of nylon membranes to which different antibodies, each specific to a different antigen, have been immobilized. Thus, the device might be utilized to test for two totally different conditions. Moreover, as is also understood by those of skill in the art, one of the elements 42 or 44 might be utilized to test for a condition and the other might be utilized as a control. Furthermore, there is no limitation as to the number of elements 42, 44 to be placed beneath opening 18a other than the physical size of the device and other such physical constraints. Thus, the device of the invention might include means for testing for a multiplicity of conditions, each causing respective analytes to be present in the same specimen. Moreover, a given test procedure might require a multiplicity of controls, each requiring a different element such as 42, 44 to be disposed beneath a respective flow director port.

Generally speaking, as is well known to those skilled in the art to which the present invention pertains, and as has been fully explained in the disclosures of the '901 patent and the '285, '240 and '158 co-pending applications identified above, the formation of coloration on the surface of element 42 and/or element 44 provides an almost instantaneous indication of the results of the assay, whether the same involves a metal sol tag in accordance with the procedure disclosed in the '285 Cole et al. application, or an enzyme tag and an immobilized antibody, such as is disclosed in U.S. Pat. No. 4,407,943. Such instantaneous coloration can be observed simply by separating barrel 14 from base 16. Thus, when the device 10 is opened to expose element 12 as illustrated in FIG. 5, the color indicating a positive or negative result will appear in the vicinity of hole 48 and/or hole 50. It is important to note in this respect that filter 52 is preferably attached to and carried by barrel 14 so that filter 52 and the debris thereon may be moved out of the way when the device is opened to read the results of the test. Thus, filter 52 need not be handled individually. Moreover, when the device is opened to read the results, swab 54 remains encased by barrel 14 and thus the device and the swab may be discarded without the need for handling the swab separately.

An alternative device which embodies the concepts and principals of the present invention is illustrated in FIGS. 6 through 10 and is designated therein by the reference numeral 110. Device 110 includes a sensitive element 112 which serves a purpose that is essentially the same as the purpose of sensitive element 12 of device 10. Device 110 is particularly useful for conducting an immunoassay procedure; however, like device 10, the exact type of procedure or protocol utilized in connection with device 110 is unimportant for purposes of the present invention other than that device 110 may be used to facilitate any sort of procedure which results in the production of a specific signal when an analyte or a derivative of an analyte is brought into contact with a contact element that is specifically sensitive to the presence of the analyte or derivative. In this regard, device 110 may be utilized in connection with all of the procedures described above for which device 10 may be utilized.

In its preferred form, device 110 may comprise a generally spool shaped guide member in the form of a spool 114 and a base component 116. Spool 114 includes internal structure defining an elongated passageway 118 extending therethrough. Passageway 118 includes a generally frusto-conically shaped chamber 120 at the upper end of spool 114, a ribbed section 124 which has a function essentially the same as ribbed section 24 of device 10 as explained above, and a section 126 which is circular in cross-sectional configuration.

Figure 8:
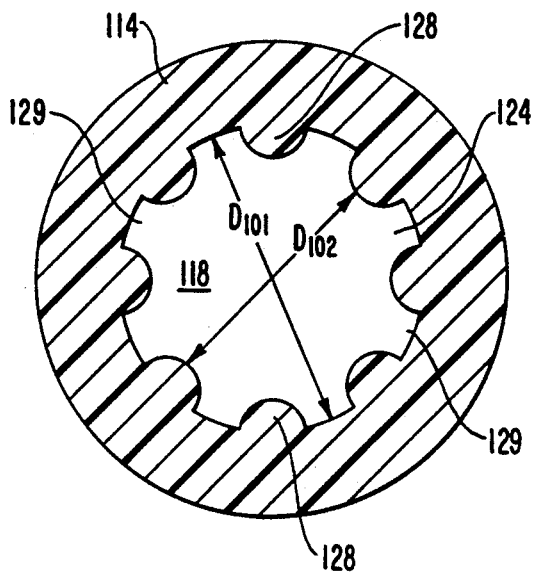
FIG. 8 is a cross-sectional view taken along the line 8—8 of FIG. 7.

With reference to FIG. 8, it can be seen that the cross-sectional configuration of section 124 presents a plurality of circumferentially spaced ribs 128. The cross-sectional configuration of section 124 is constant and thus ribs 128 extend along passageway 120 from the upper end 124a of section 124 to the lower end 124b thereof. Also, as can be seen viewing FIG. 8, ribs 128 are uniformly distributed around the circumference of the passageway and the same are configured to present channels 129 therebetween. Channels 129, like ribs 128, extend along the passageway from the upper end 124a of section 124 to the lower end of 124b thereof. Ribs 128 thus present means projecting radially inwardly of passageway 118 to restrict the cross-sectional area thereof.

Figure 7:
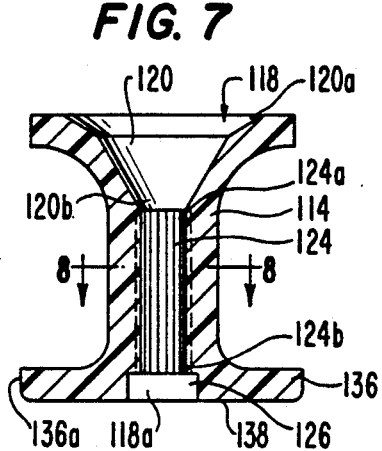
FIG. 7 is an enlarged, cross-sectional, elevational view of the guide member of the embodiment of FIG. 6.

As can be seen viewing FIG. 7, chamber 120 has an upper or outer opening 120a that is larger in cross-sectional dimension than the opening 120b at the lower end of chamber 120.

Figure 9:
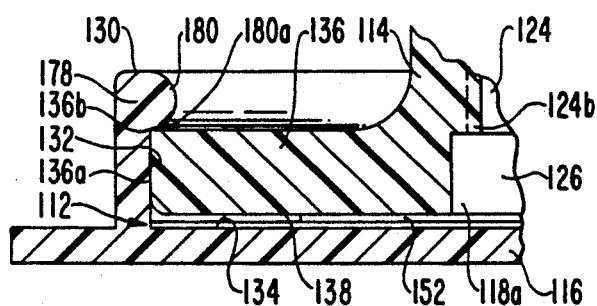
FIG. 9 is a partial, cross-sectional, elevation view taken along the line 9—9 of FIG. 6 to illustrate the constructional details of and the operational relationships between the guide member, the base component and the sensitive element.
Figure 10:
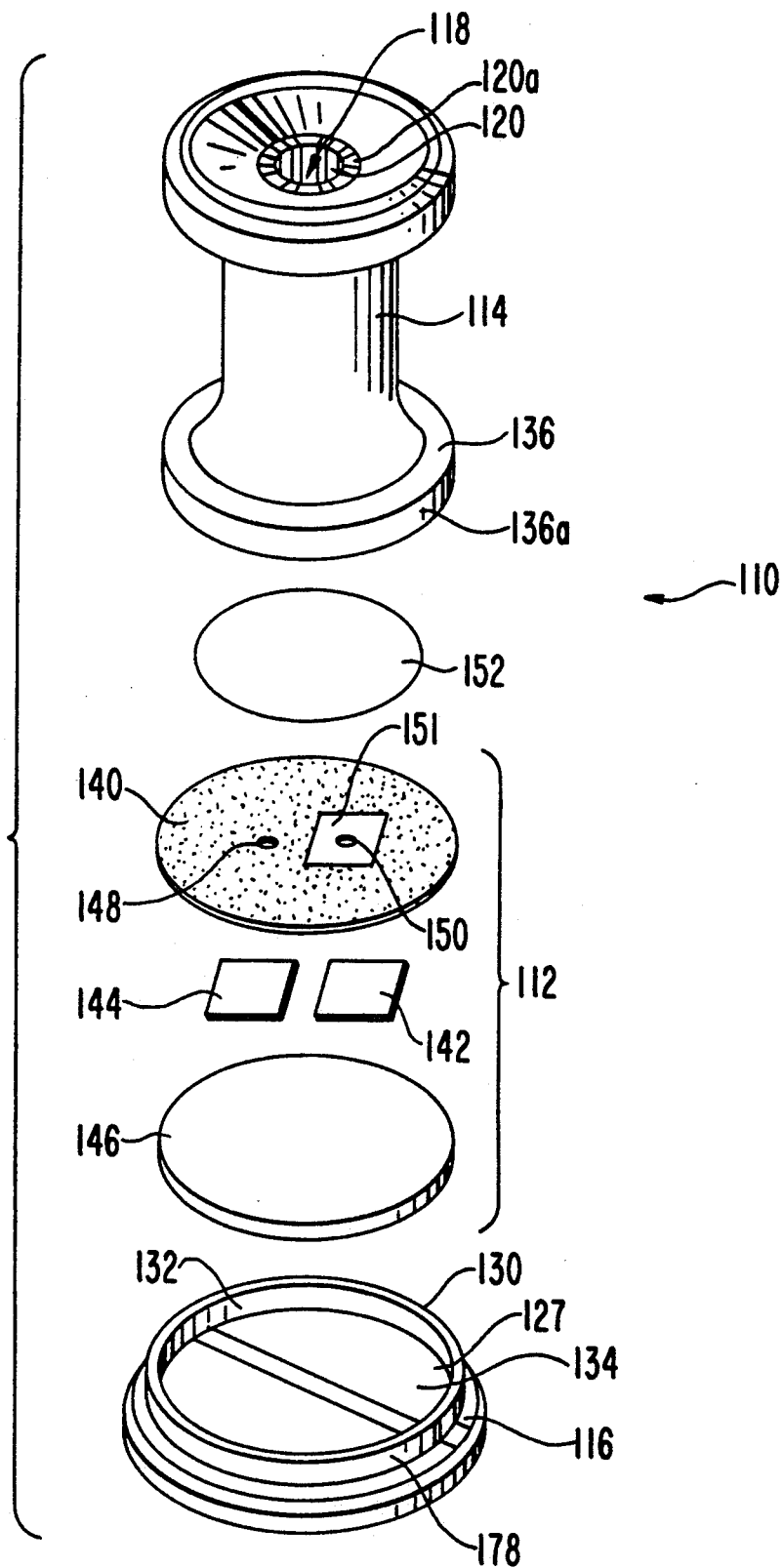
FIG. 10 is an enlarged, exploded schematic, isometric view of the device of FIG. 6 to particularly illustrate the components of a preferred embodiment of the sensitive element.

Spool 114 is normally mounted on base 116 during performance of a test procedure. This cooperative relationship is illustrated particularly in FIG. 9. To facilitate such mounting, base 116 is provided with a circular test well 127 which opens upwardly of the upper surface 130 of base 116. Well 127 is defined by a generally circular internal side wall 132 and a floor 134. As can be seen in FIGS. 9 and 10, a sensitive element 112 is mounted on or carried by floor 134 in well 127 of base 116 when the test device assembled in its operable condition.

As can be seen viewing FIGS. 6, 7, 8 and 10, the lower end of spool 114 is in the form of a flange 136 which presents a projection that projects into well 127 when spool 114 is mounted in operating disposition on base 116. Flange 136 presents an outer cylindrical external surface 136a which is disposed in close proximity to wall 132 when flange 136 is received within well 127. The undersurface of flange 136 provides spool 114 with a distal end 138 which is disposed in immediate proximity relative to element 112 when spool 114 is mounted on base 116 in its operating disposition.

A prefilter 152 is attached at distal end 138 of spool 114 in covering relationship to the lower end 118a of passageway 118.

Device 110, like device 10 described above, may be utilized for conducting an immunoassay test in conjunction with a swab 154 which comprises an elongated stick 156 and an absorbent or porous tip 158. In performing a test procedure, swab tip 158 is pushed downwardly through passageway 118 and toward element 112. Thus, swab 154 will assume a position relative to device 110 which is essentially the same as the position of swab 54 relative to device 10 as illustrated in FIG. 4.

As can be seen viewing FIGS. 9 and 10, base 116 comprises a ring portion 178 which extends around well 27. As can be seen, the inner surface of ring 178 presents wall 132 which, along with floor 134 defines well 127. In FIG. 9 it can be seen that an annularly shaped lip 180 extends around well 127 at the upper extremity of wall 132. Lip 180 has an inner diameter which is slightly less than the outer diameter of surface 136a of flange 136. Additionally, ring 178 has sufficient resiliency to allow lip 180 to move out of the way of flange 136 as the latter is positioned in well 127. Thus, the peripheral portions of flange 136 and lip 180 provide a snap fit to releasably hold distal end 138 of spool 114 in well 127 and in close proximity to sensitive element 112, all as is illustrated in FIG. 9. In this regard, in the preferred form of the invention, when the ring 178 snaps back into place as flange 136 is inserted into well 127, the curvature of the lower surface 180a of lip 180 presents a camming surface which interacts with the upper edge 136b of flange 136 to resiliently urge the spool 114 toward floor 134 and force filter 152 into intimate capillary contact with element 112.

As indicated above, spool 114 is normally mounted on base 116 in covering relationship to element 112 during the conduct of a test procedure. The peripheral portion 136b of flange 136 is complimentarily and correspondingly shaped so as to cooperate with camming surface 180a of lip 180 to urge flange 136 toward element 112 and provide a mated, snap fit relationship between spool 114 and base 116. Spool 114 and base 116 are therefore normally releasably held together with spool 114 disposed in covering relationship to element 112 during the conduct of a test procedure. On the other hand, the snap fit between the peripheral portions of flange 136 and lip 180 is such that spool 114 may readily be separated from base 116 at the conclusion of the test procedure to permit element 112 to be visually inspected.

Spool 114 and base 116 may be constructed of plastic or glass or any other suitably inert material, and these components may be made by injection molding of a thermoplastic material such polyethylene or polystyrene. In the preferred form of device 110, spool 114 may be molded from a polystyrene material and base 116 may be molded from a polyethylene material. The only real limitations on the materials of construction for device 110 is that the device must have structural stability and sturdiness and the same must be inert to the test reactants and the reaction products.

In a preferred form of the invention, as indicated above, device 110 may be utilized for conduct of an immunoassay procedure. Thus, element 112 serves exactly the same purpose and may be essentially the same as element 12 and the various forms thereof described above in connection with device 10. Also, prefilter 152 serves the same function and may be identical with prefilter 52 as described above. Thus, prefilter 152 may be held in place on the distal end 138 of spool 114 using an adhesive or by ultra-sonic welding, etc.

In operation device 110 operates in essentially the same manner as device 10. In this regard, a specimen is collected on absorbent tip 158 of swab 154 and swab tip 158 which has the absorbed reaction mixture thereon is then inserted into device 110. To facilitate such insertion, chamber 120 serves the same purpose as chamber 20. And generally speaking, the various components of device 110 serve essentially the same purpose as the correspondingly numbered components of device 10. By correspondingly numbered it is simply meant that the components of device 110 are identified by reference numerals in the 100 series and thus a component of device 110 identified, for example, by the reference numeral 116, corresponds with a component of device 10 which is identified by the reference numeral 16. Thus, as swab 154 is manually pushed downwardly through passageway 118 utilizing stick 156 which extends outside of spool 114, tip 158 is directed toward element 112. Ribs 128 in section 124 of passageway 118 provide means adjacent end 118a of passageway 118 for squeezing swab tip 158 to express fluid therefrom as tip 158 is pushed downwardly toward element 112. Channels 129 prevent the liquid in swab tip 158 from welling up and thus facilitate the flow of expressed fluid downwardly through prefilter 152 and toward element 112.

In contrast to the length of ribs 28 in device 10, ribs 128 of device 110 have a length which is approximately 1½ times the length of the swab tip. With reference to FIG. 8, the major cross-sectional dimension $D_{101}$ of section 124 of passage 118 at the bottoms of channels 129 may preferably be approximately 0.210 inch and the minor dimension $D_{102}$ measured at the apex of each rib 128 may be approximately 0.169 inch to thus accommodate a conventional swab 154 having an absorbent tip 158 having a diameter of approximately 0.1875 inch. In this same connection, and viewing FIG. 7, spool 114 may have an elevational dimension of 1.00 inch, flange 136 may have an outer diameter at surface 136a of 1.00 inch and well 127 may correspondingly have an inner diameter of approximately 1.00 inch. Additionally, section 126 of passageway 118 may be circular and have a diameter of approximately 0.250 inch. The central body portion of spool 114, as illustrated in FIG. 8, may have an outside diameter of approximately 0.399 inch. Finally, flange 136 may preferably be 0.100 inch in elevational thickness as illustrated in FIGS. 7 and 9.

Just as in the case of device 10, as tip 158 of swab 154 is pushed into intimate contact with filter 152, which covers the end of passageway 118, absorbent tip 158 is essentially in direct capillary communication with assemblage 112. Thus, liquid is expressed from tip 158 by the pressure exerted by ribs 128 and the manual pressure on stick 156 pushing tip 158 against filter 152. The expressed liquid is channeled by channels 129 of passageway 118 and by passageway section 126 so that the same flows through filter 152 and then through element 112.

Figure 6:
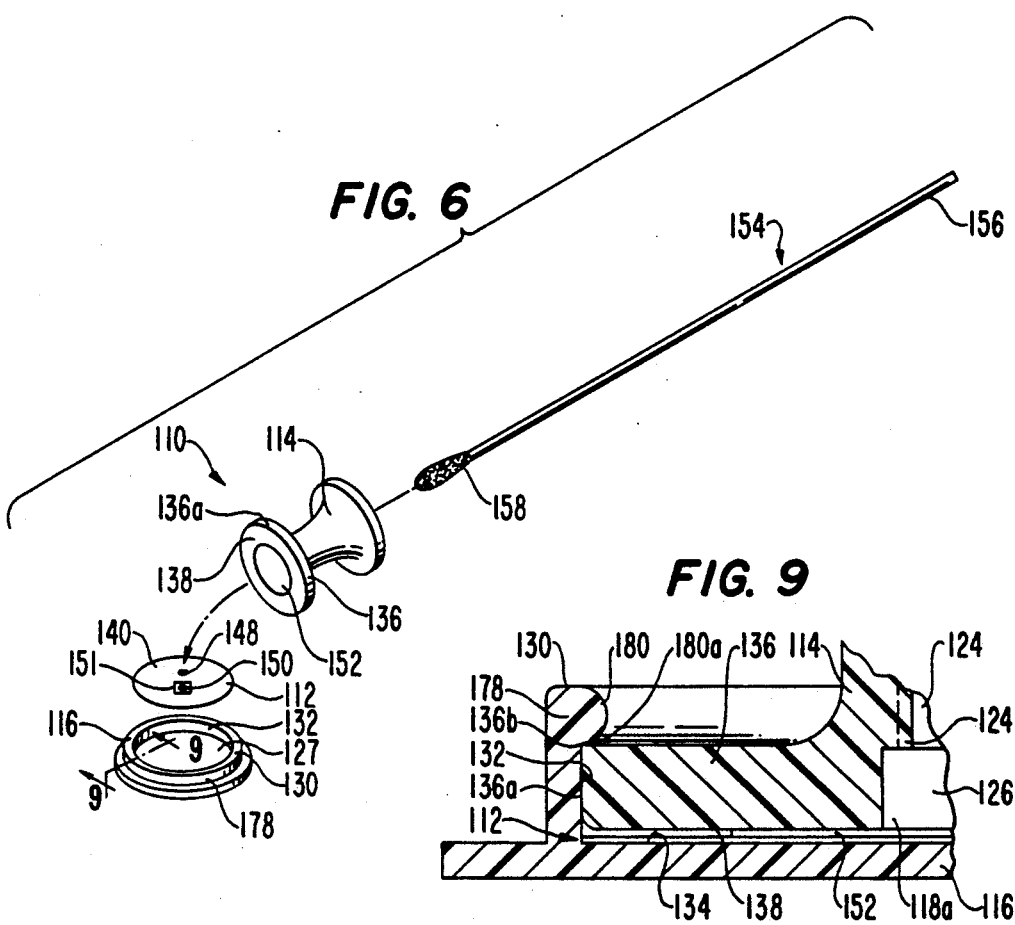
FIG. 6 is an exploded, isometric view illustrating an alternative disposable, pre-packaged device which embodies the principles and concepts of the present invention.

In the format of the invention described above in connection with device 10 and its sensitive element 12, flow director 40 may be constructed of a transparent non-porous flexible sheet material such as polyester film with the port 50 providing a test zone and the port 48 providing a positive or negative control zone. When flow director 40 is transparent, membranes 42 and 44 are fully exposed to view and the test result, which tends to spread through membranes 42 and 44, is readily viewable but interpretation may be ambiguous to the untrained eye due to the complexity of the visual field. When an opaque material is used to construct director 40, the field of the test result is cleaner and more sharply defined; however, low background levels from negative samples sometimes appears positive against the contrasting color of the director 40. As is also described above, element 112 generally may be identical to element 12. However, in a particularly preferred format for sensitive element 112, as is illustrated in FIGS. 6 and 10, flow director 140 may preferably be white and opaque and a transparent window 151 may be provided around port 150. As is shown particularly in FIG. 10, window 151 is square; however, the exact shape of the window is not critical. Thus, a defined portion of membrane 144 is exposed to view beneath window 151 to act as a negative background reference and alleviate false positive results.

Manifestly, it is within the contemplation of the invention that the flow director 40 of device 10 may also be opaque and include a transparent window (such as the window 151) around port 50, to alleviate false positive results.

It will be readily apparent to those of ordinary skill in the art, that while the device of the present invention has been described in connection with certain specific immunoassay procedures, the same might also be utilized in connection with other immunoassay procedures that involve a liquid phase reaction and production of a labelled immunoreaction product that is capturable on a porous media capture element, either by a filtration process or an immunochemical reaction. In this regard, capture elements 42 and 44 and of device 10 elements 142 and 144 forming a part of device 110, may be filter elements having pores of a size to prevent passage of a desired collectible reaction product, or porous elements, such as microporous membranes, to which is bound an immunoreactive substance that is specifically reactive in the desired immunoassay reaction.

Additionally, the devices 10 and 110 described above might be used in connection with any liquid sample containing an analyte to be tested for, so long as the element 12 or the element 112, as the case may be, includes a material which is specifically sensitive to the analyte to provide an indication of the presence of the analyte in the liquid sample. Thus, the device of the invention might well be adapted for use in conducting a purely chemical test rather than the immunochemical test described above.

Finally, although the devices 10 and 110 have been described above as being particularly useful for applications involving a swab borne analyte, the devices 10 and 110 might also be used in applications where a liquid containing the analyte or derivative thereof is simply poured through the passageway 18 or 118 as the case may be. In this connection, the prefilter 52, 152 is disposed in intimate capillary contact with the test element 12, 112 for filtering out undesired materials during the conduct of the test and upon completion of the test the removability of the guide member 14, 114 and filter 52, 152 from base 16, 116 facilitates the viewability of the test elements 12, 112 and the evaluation of the test results.

We claim:

1. A disposable kit for conducting an assay test, said kit comprising:
   a swab comprising an elongated stick and an absorbent tip at one end of the stick for carrying a fluid material containing an analyte or derivative thereof;
   a base component;
   a contact element mounted on the base component, said element being sensitive to the presence of an analyte or derivative thereof which comes into contact therewith;
   a guide member for mounting on the base component over the contact element, said member being removable from the base component so as to permit inspection of the contact element,
   said guide member having an elongated passageway extending therethorugh, said passageway having a first open end that is positioned adjacent the contact element when the member is mounted on the base component, said passageway having a second open end that is spaced from said first open end, said second open end constructed so as to open outwardly of the kit when the member is mounted on the base component,
   said passageway including funnel means at said second open end thereof so as to receive the tip of said swab said funnel means further being constructed so as to guide said tip into the passageway as the stick is manually pushed through the passageway and toward said first end thereof; and
   squeeze structure located in the passageway adjacent said first end so as to contact the swab tip when said manually pushed swab stick and said tip are being pushed through the passageway and toward the contact element, so as to cause the tip to be squeezed such that fluid material is expressed therefrom.

2. A kit as set forth in claim 1, wherein said passageway is generally circular in cross-sectional configuration and said squeeze structure comprises projection means which protrude in a radially inward direction into the passageway so as to restrict the cross-sectional area of the passageway.

3. A kit as set forth in claim 2, wherein said projection means comprises a plurality of ribs spaced circumferentially around the passageway, each rib extending along the passageway.

4. A kit as set forth in claim 3, wherein said ribs are uniformly distributed around the circumference of the passageway and wherein each rib has a length which is approximately 1½ of the overall length of the swab tip.

5. A kit as set forth in claim 3, wherein said ribs are constructed and arranged so as to define channels therebetween extending along the passageway to facilitate flow of expressed fluid toward the contact element.

6. A kit as set forth in claim 1, wherein said funnel means comprises means defining a generally conically shaped tip receiving chamber having an outer opening which is larger in diameter than the swab and a smaller inner opening.

7. A kit as set forth in claim 1, further including a prefilter carried by said guide member in a position so as to cover said first open end of the passageway.

8. A kit as set forth in claim 1, wherein said base component and said guide member include releasable means for holding the base component and guide member together during testing and permitting separation of the same at the completion of a test.

9. A kit as set forth in claim 8, wherein said releasable means defines a well in the base component and a complimentarily shaped projecting portion on the guide member, said projecting portion being received in the well and held in place by frictional engagement.

10. A kit as set forth in claim 9, wherein the well is further defined by a sidewall and a floor, and the complimentarily shaped projecting portion has an external surface and a distal end, said contact element being mounted on the floor of the well and said first open end of the passageway being disposed at said distal end of said portion, said frictional engagement being between said sidewall and said external surface.

11. A kit as set forth in claim 10, wherein said well is generally circular and said surface is cylindrical.

12. A kit as set forth in claim 10, further including vent means for venting air from the well.

13. A kit as set forth in claim 12, wherein said vent means comprises a groove extending from the floor and along the sidewall of the well.

14. A disposable kit for conducting an immunoassay, said kit comprising:
   a swab comprising an elongated stick and an absorbent tip at one end of the stick for carrying a fluid material containing an immunoreactive constituent;
   a base component having an upper surface and including an internal sidewall and a floor defining a test well that opens upwardly of said upper surface;
   a contact element disposed on said floor, said element being sensitive to the presence of an immunoreactive constituent with which said element comes into contact therewith;
   a guide member including a projecting portion having an outer surface, said guide member being shaped so as to communicate with the internal sidewall of the base, said portion being positioned within said well with its outer surface engaging the internal sidewall of the base, and being removable from the base for visual inspection of the contact element, said guide member having an elongated passageway extending through said portion, said passageway having a first open end that is positioned adjacent the contact element so as to open toward the contact element when said portion is positioned in the well, said passageway having a second open end that is spaced from said first end so as to open upwardly of the device when said portion is positioned in the well, said passageway including funnel means located at said second open end thereof so as to receive the tip of said swab, said passageway further being constructed so as to guide said tip into and through the passageway and toward said first open end thereof by manually pushing said stick of said swab, said passageway comprising means for directing the swab tip of said manually pushed stick toward the contact element; and squeeze structure located in the passageway adjacent said first open end thereof so as to contact said swab tip of said manually pushed stick, said squeeze structure being constructed so as to squeeze said tip to express fluid material therefrom.

15. A kit as set forth in claim 14, further including a prefilter attached to the projecting portion in a position so as to cover said first open end of the passageway.

16. A kit as set forth in claim 14, wherein the internal sidewall of said well is circular and the external surface of said projecting portion is cylindrical in shape.

17. A kit as set forth in claim 14, wherein said base component and said guide member are each molded from thermoplastic material.

18. A kit as set forth in claim 17, wherein the sidewall of said well and the external surface of said projecting portion are each cylindrical in shape.

19. A kit as set forth in claim 18, wherein the external surface of the projecting portion and the sidewall of the well cooperate to provide a frictional fit so as to hold the projecting portion in the well.

20. A kit as set forth in claim 14, wherein the external surface of the projecting portion and the sidewall of the well cooperate to provide a frictional fit so as to hold the projecting portion in the well during the conduct of test procedures.

21. A kit as set forth in claim 14, further including means on the external surface of the projecting portion and on the internal sidewall of the well for venting the well.

22. A kit as set forth in claim 14, wherein said passageway is generally circular in cross-sectional configuration and said squeeze structure comprises projection means which protrude in a radially inwardly direction into the passageway so as to restrict the cross-sectional area of the passageway.

23. A kit as set forth in claim 22, wherein said projection means comprises a plurality of ribs spaced circumferentially around the passageway, each rib extending along the passageway.

24. A kit as set forth in claim 23, wherein said ribs are uniformly distributed around the circumference of the passageway and each rib has a length which is approximately $\frac{1}{2}$ of the overall length of the swab tip.

25. A kit as set forth in claim 23, wherein said ribs present channels therebetween extending along the passageway to facilitate flow of expressed fluid toward the contact element.

26. A kit as set forth in claim 24, wherein said funnel means comprises means defining a generally conical shaped tip receiving chamber having an outer opening which is larger in diameter than the swab tip and a smaller inner opening.

27. A kit as set forth in claim 1, wherein said base component and said guide member are each molded from a thermoplastic material.

28. A kit as set forth in claim 14, wherein said element comprises a porous capture membrane.

29. A kit as set forth in claim 28, wherein an immunoreactive component is attached to said membrane.

30. A kit as set forth in claim 28, wherein the pores of said membrane are of a size to prevent passage of an immunocomposite created.

31. A kit as set forth in claim 8, wherein said releasable means comprises a well in the base component and a flange portion on the guide member, said flange portion being received in the well, said well further comprising an inwardly extending lip disposed around the well, said lip and said flange portion cooperating when the flange portion is in the well so as to releasably hold the guide member in place during operation of the device and permit removal of the guide member such that the contact element may be inspected.

32. A kit as set forth in claim 31, wherein said flange portion is circular and said lip is annular.

33. A kit as set forth in claim 17, wherein said guide member is cylindrical in shape.

34. A kit as set forth in claim 17, wherein said guide member is generally spool shaped.

* * * * *

UNITED STATES PATENT AND TRADEMARK OFFICE
CERTIFICATE OF CORRECTION

PATENT NO. : 5,084,245

DATED : January 28, 1992

INVENTOR(S) : CARL M. BERKE et al.

It is certified that error appears in the above-identified patent and that said Letters Patent is hereby corrected as shown below:

Column 3, line 44, "o" should be --on--.

Column 6, line 49, "crosssectionel" should be

--cross-sectional--.

Signed and Sealed this

Twenty-fifth Day of May, 1993

Attest:

MICHAEL K. KIRK

Attesting Officer

Acting Commissioner of Patents and Trademarks